United States Patent [19]
Pelley et al.

[11] Patent Number: 5,766,388
[45] Date of Patent: Jun. 16, 1998

[54] PROCESS FOR FORMING LAMINATED ABSORBENT STRUCTURES HAVING REDUCED DELAMINATION TENDENCIES

[75] Inventors: Kenneth Pelley, Hopewell; Lynn Foelsch, Hillsborough; William M. Bickley, Edison, all of N.J.

[73] Assignee: McNeil-PPC, Inc., Skillman, N.J.

[21] Appl. No.: 811,184

[22] Filed: Mar. 4, 1997

Related U.S. Application Data

[63] Continuation of Ser. No. 350,920, Dec. 7, 1994, abandoned.

[51] Int. Cl.⁶ .................. A16F 13/00; B32B 31/00
[52] U.S. Cl. ............ 156/62.6; 156/62.2; 156/204; 156/276; 156/285; 19/301; 19/304; 264/112; 264/121; 264/518
[58] Field of Search .................. 19/296, 301, 302, 19/304; 425/81.1, 83.1; 156/276, 202, 204, 62.2, 285, 62.6; 264/112, 121, 518

[56] References Cited

U.S. PATENT DOCUMENTS

| | | |
|---|---|---|
| 3,766,922 | 10/1973 | Krusko. |
| 4,023,570 | 5/1977 | Chinai et al.. |
| 4,560,379 | 12/1985 | Stemmler. |
| 4,675,209 | 6/1987 | Pedigrew. |
| 5,213,817 | 5/1993 | Pelley. |
| 5,395,359 | 3/1995 | Nakanishi et al.. |
| 5,415,717 | 5/1995 | Perneborn. |
| 5,460,623 | 10/1995 | Emenaker et al.. |

FOREIGN PATENT DOCUMENTS

| | | |
|---|---|---|
| 0 463 716 A2 | 4/1991 | European Pat. Off.. |
| 0 478 182 A1 | 9/1991 | European Pat. Off.. |
| 0 509 409 | 4/1992 | European Pat. Off.. |
| 025714/191 | 1/1991 | Japan. |
| 2 124 499 | 4/1983 | United Kingdom. |
| 2 133 291 | 1/1984 | United Kingdom. |
| 2 157 570 | 4/1985 | United Kingdom. |
| 2 255 720 | 11/1992 | United Kingdom. |
| WO 85/02110 | 5/1985 | WIPO. |
| WO 94/02092 | 2/1994 | WIPO. |

*Primary Examiner*—Jeff H. Aftergut
*Assistant Examiner*—Sam Chuan Yao

[57] ABSTRACT

The present invention utilizes the smooth continuous motion of a masking belt to concentrate air-entrained absorbent materials on the surface of a moving fibrous substrate. Air flowing through the open areas of the masking belt carries the entrained material into the fibrous web. The fibrous web acts as a filter to separate the entrained material from the air stream. Substantially all dispensed material is captured by the fibrous web, and expensive and complex absorbent material recycle systems can be eliminated.

11 Claims, 4 Drawing Sheets

PROCESS FOR FORMING LAMINATED ABSORBENT STRUCTURES HAVING REDUCED DELAMINATION TENDENCIES

This is a continuation of application Ser. No. 08/350,920, filed Dec. 7, 1994, now abandoned.

FIELD OF THE INVENTION

The present invention relates to a process for forming laminated absorbent structures having reduced delamination tendencies and to products made by this process. The process provides for the application of additional absorbent material to a fibrous substrate in discrete zones. The resulting structures have improved integrity.

BACKGROUND OF THE INVENTION

The manufacturers of inexpensive absorbent structures such as diapers, adult incontinence guards and pads, sanitary napkins, and panty liners are increasingly looking to the use of laminated absorbent structures to improve processing. Examples of such laminated absorbent structures are described in Chinai et al., U.S. Pat. No. 4,023,570; Seidy, U.S. Pat. No. 4,862,574; Luceri, EP-A-0 597 273; and the like. These structures incorporate absorbent layers which are generally made by air-laying fibers to form a continuous web. These absorbent layers may provide the majority of the absorbent capacity of the product, or they may be supplemented by additional absorbent materials.

Therefore, the incorporation of additional absorbent materials to the absorbent layers of laminated products is increasingly important. It is particularly difficult to manage the application of powdered, granular, particulate, and short fibrous absorbent materials. Examples of processes to apply such additional materials include Pelley, U.S. Pat. No. 5,213,817, and Kock et al., U.S. Pat. No. 4,551,191.

Kock discloses a method for uniformly distributing discrete particles on a moving porous web. It involves mixing particles within a moving airstream to provide a uniform distribution, and directing the particles out of a nozzle in a direction substantially parallel to the movement of the porous web. A pressure differential across the porous web is established and maintained in an area which coincides with the width of the particle discharge nozzle. Thus, the bulk of the discharged particles are substantially uniformly deposited onto the uppermost surface of the moving porous web.

Pelley discloses an apparatus for intermittently applying a particulate powder material to a moving fibrous substrate. Particles are dispensed from a hopper into an air stream. The resulting air-entrained particles are directed out of a nozzle which oscillates between first and second positions. In the first position, particles are applied to a predetermined location on the moving substrate, and in the second position, the particles are recirculated to the particle feed hopper. However, further improvements are needed to allow the controlled application of additional absorbent materials to discrete portions of a fibrous substrate.

An object of the present invention is to provide a process for smoothly depositing absorbent materials in a discrete pattern of fill and void areas onto a moving fibrous substrate. Another object of the present invention is to increase equipment simplicity, to provide high-speed pattern formation, and to provide repeatable, uniform patterns of absorbent material on a moving fibrous substrate.

SUMMARY OF THE INVENTION

The present invention utilizes the smooth continuous motion of a masking belt to concentrate air-entrained absorbent materials on the surface of a moving fibrous substrate. Air flowing through the open areas of the masking belt carries the entrained material into the fibrous web. The fibrous web acts as a filter to separate the entrained material from the air stream.

Improved laminated absorbent structures can be manufactured according to the present invention. This invention relates to a continuous process for forming a laminated absorbent structure having reduced delamination tendencies. To practice this invention, one moves a fibrous substrate having lateral sides, a longitudinal axis, a first major surface, and a second major surface, opposite the first, the second major surface defined by a cover layer through a manufacturing zone having a pressure differential across the moving fibrous substrate. In this zone, the fluid pressure acting on the first major surface is greater than the fluid pressure acting on the second major surface. Thus, air is drawn through the fibrous substrate. While air is being drawn through the substrate, at least a portion of the second major surface is masked to prevent to air flow therethrough, and a metered amount of an absorbent material is provided to the first major surface in a pattern corresponding to the unmasked portion of the second major surface. At least a portion of the absorbent material can be densified to contain the absorbent material within the resulting absorbent structure. Additional process steps may include applying an adhesive to the first major surface to provide for lamination of additional layers or for the folding of the fibrous substrate.

One possible product of this invention is a laminated absorbent structure having reduced delamination tendencies. This structure includes a fibrous substrate having a first major surface and a second major surface, opposite the first, the second major surface defined by a cover layer. An adhesive composition is adhered to at least a portion of the first major surface of the fibrous substrate, and an absorbent material is at least partially immobilized by the adhesive composition and is disposed in a pattern to form at least one discrete absorbent material-containing zone which occupies less than 100% of the first major surface of the fibrous substrate and at least one absorbent material-free zone. The absorbent material is contained within the absorbent structure by at least the cover layer and at least one peripheral densification of the fibrous substrate in the at least one absorbent material-free zone. The fibrous substrate may be folded to fully enclose the absorbent material, or it may be covered by additional laminated layers. Because the densified areas are substantially free of the absorbent material, they are less likely to delaminate as this material absorbs substantial amounts of fluids and expands.

DETAILED DESCRIPTION OF THE PREFERRED EMBODIMENT

The present invention utilizes the smooth continuous motion of a masking belt to concentrate air-entrained absorbent materials on the surface of a moving fibrous substrate. Air flowing through the open areas of the masking belt carries the entrained material into the fibrous web. The fibrous web acts as a filter to separate the entrained material from the air stream.

Figure 1:
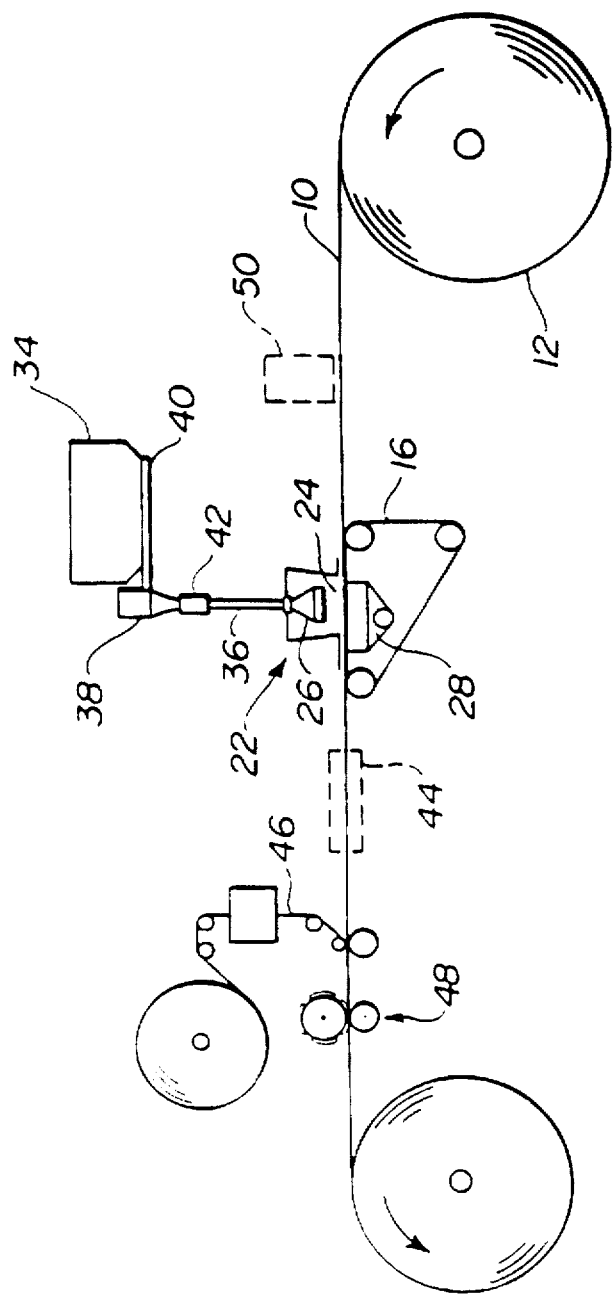
FIG. 1 is a side elevation illustrating the process of the present invention.
Figure 2:
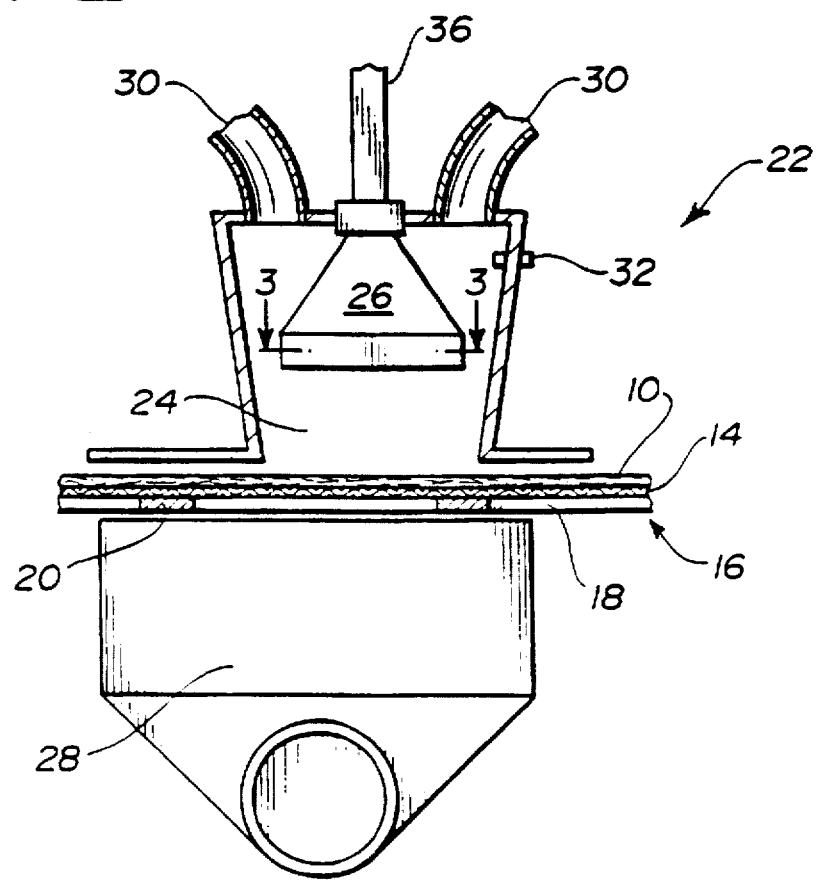
FIG. 2 is a side elevation of a forming chamber useful in the process of the present invention.
Figure 3:
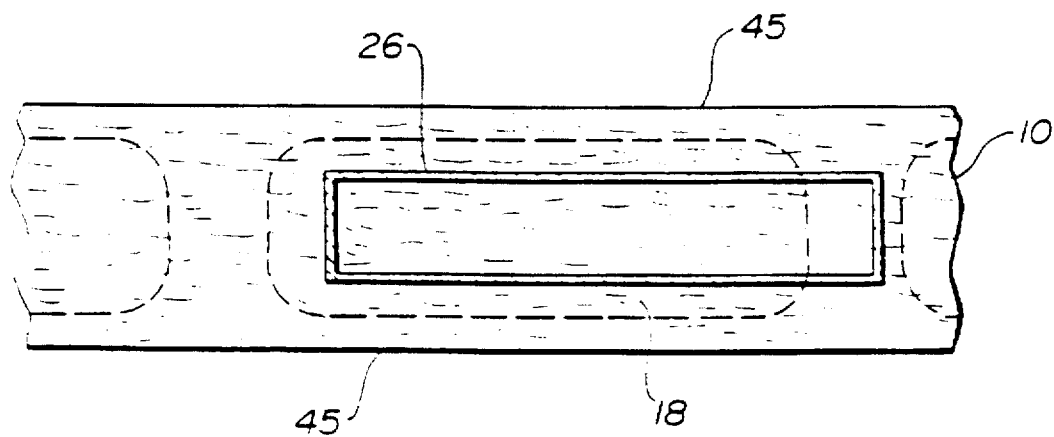
FIG. 3 is a view along line 3—3 of FIG. 2, illustrating the relationship between a dispensing nozzle, a fibrous substrate, and a masking belt useful in the present invention.

Referring to FIGS. 1–3, the present invention relates to a process for forming absorbent structures. In the practice of the invention, a fibrous substrate 10 is unwound from a supply roll 12 onto a moving carrier screen 14. Preferably, the fibrous substrate 10 includes a cover fabric layer and an air-laid fibrous layer. The carrier screen 14 moves over a masking belt 16 having void areas 18 and mask areas 20. The substrate 10, carrier screen 14, and masking belt 16 then move into a forming station 22.

The forming station 22 includes a forming chamber 24, an absorbent material supply nozzle 26, and a vacuum chamber 28. The forming station 22 may also include an air supply 30 to maintain a controlled atmospheric pressure in the forming chamber 24 and a sensor 32 to monitor this pressure. The material supply nozzle 26 is operatively connected to an absorbent material supply feeder 34 by means of, e.g., conduit 36.

In a preferred embodiment, the supply feeder 34 transfers absorbent material into a supply hopper 38 via a screw auger 40. The absorbent material is drawn through a venturi 42 to entrain the material in an air stream. The air-entrained material is delivered through the conduit 36 to the supply nozzle 26. From the supply nozzle 26, the air entrained material is drawn through the forming chamber 24 and onto the moving fibrous web 10 in a discrete pattern. The pattern of absorbent material deposition corresponds to the void areas 18 of the masking belt 16. This occurs as there is an atmospheric pressure differential between the forming chamber 24 and the vacuum chamber 28. Thus, the air will tend to flow through portions of the fibrous web 10 corresponding to the void areas 18 of the masking belt 16. Again, the fibrous web 10 will tend to catch the entrained material to result in discrete areas of the fibrous web 10 having the absorbent material deposited thereon.

The forming station 22 of the present invention greatly reduces the amount of absorbent material which by-passes the moving web 10. Thus, absorbent material need not be recycled in the present process. Absorbent material recycling systems are typically a process and maintenance problem in current particulate absorbent dispensing systems. The mechanical complexity of the resulting system is greatly reduced. However, if desired, a recyling system could be included in the present process.

From the forming station 22, the fibrous web 10 can continue on for further processing such as folding of the fibrous substrate 10 at a folding station 44, application of a barrier layer 46, densification of the fibrous substrate 10 in regions corresponding to the mask areas 20 of the masking belt 16 to contain the absorbent material within the resulting absorbent product at a densification station 48, and cutting individual absorbent products from the continuous web 10 (not shown). The operation of these processes is well known to those of ordinary skill in the art.

In further detail, the lateral sides 45 can be folded parallel to the longitudinal axis of the moving web 10 in the folding station 44. Preferably, both lateral sides 45 are folded and meet at the longitudinal axis to fully enclose the first major surface of the moving web 10 on which the absorbent material has been deposited. This can be described as a c-folding process.

In the barrier layer 46 station, a web of release paper can be continuously coated with a hot melt pressure sensitive adhesive (PSA). This positioning adhesive is brought into contact with the barrier layer 46, and the construction is nipped to transfer the adhesive to the barrier layer 46. The opposite side of the release paper is then coated with a construction adhesive, preferably another hot melt PSA, and the barrier layer 46 is adhered and nipped to the moving web 10.

Optional operations may include applying an adhesive pattern to the moving web 10 at an adhesive station 50. This pattern can be used to partially immobilize the absorbent material within the resulting absorbent structure and to help to secure further layers to the fibrous web 10, such as additional nonwoven layers or in the c-folding operation described above. The adhesive pattern can be applied as thin lines, wider stripes, cycloid patterns, dots, a fibril spray pattern, and the like. A preferred adhesive pattern is applied in a cycloid pattern as described in Boger, U.S. Pat. No. 4,815,660, herein incorporated by reference.

The optional pressure sensor 32 in the forming chamber 24 may be used to control the optional air supply 30 to maintain a continuous pressure differential across the moving web 10 in the forming station 22. This is useful as there is no physical seal between the forming chamber 24, the moving web 10, and the vacuum chamber 28. If the air pressure within the forming chamber 24 is too low, air may leak into the chamber 24. If the velocity of air flowing into the chamber 24 is too great, the absorbent material deposited onto the moving web 10 may be disturbed as the web 10 exits the forming chamber 24. If the air pressure within the forming chamber 24 is too high, absorbent material-laden air may leak out of the chamber 24, causing undesirable dusting of the absorbent material outside of the forming station 22. Therefore, it is helpful to have the air pressure in the forming chamber 24 slightly below atmospheric pressure outside of the forming chamber 24. Therefore, the exiting effects would be minimal.

The process of the present invention can be used to produce several different types of absorbent products. Examples of such products include panty liners, sanitary napkins, incontinence devices, diapers, absorbent pads and liners, and the like. Two embodiments of these products are illustrated in FIGS. 4–6 and 7–8, respectively.

Figure 4:
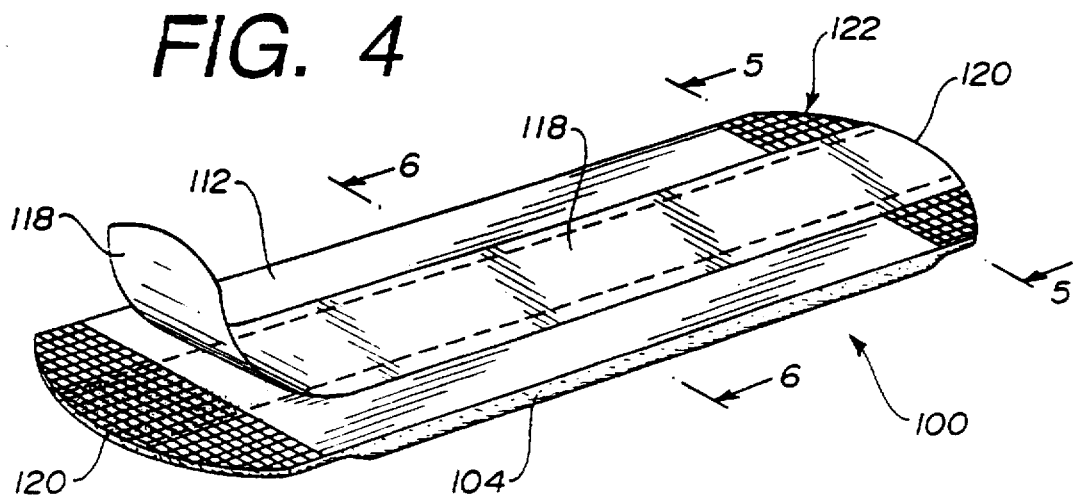
FIG. 4 is a perspective view of one embodiment of an absorbent product of the present invention.
Figure 5:
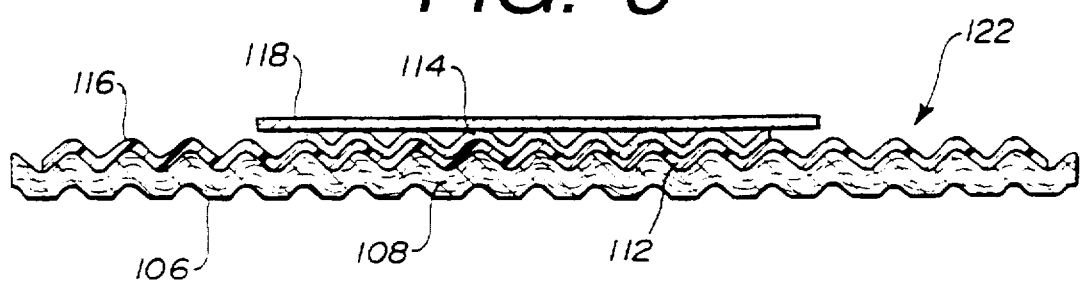
FIG. 5 is view along line 5—5 of FIG. 4, illustrating a C-folded product according to the present invention.
Figure 6:
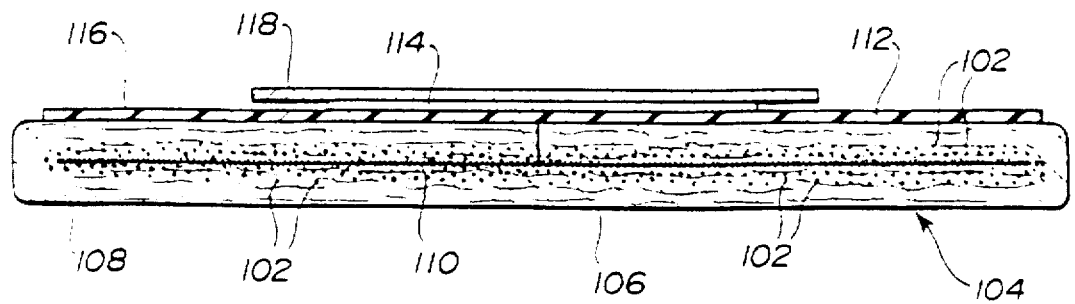
FIG. 6 is a view along line 6—6 of FIG. 4, illustrating a substantially absorbent material-free densification zone.

Referring now to FIGS. 4–6, there is illustrated a C-folded absorbent product 100 having an absorbent material 102 distributed therein. The absorbent product 100 includes an absorbent structure 104 having a cover layer 106, a fibrous layer 108, and a construction adhesive 110. The absorbent structure 104 may be adhered to a barrier layer 112 having a positioning adhesive 114 disposed upon a garment-facing surface 116 thereof. The positioning adhesive 114 may be protected by a release liner 118.

At the longitudinal ends 120 of the product 100, there are densified areas 122. These areas 122 are substantially absorbent material-free. By "substantially absorbent material-free", it is meant that there is not enough absorbent material in these areas to allow the absorbent material to cause a lamination failure as the product becomes saturated with fluids. Preferably, there is less than about 1 mg/cm$^2$, more preferably, less than about 0.4 mg/cm$^3$, and most preferably, less than about 0.03 mg/cm$^2$ of the absorbent material 102 in these densified areas 122. If there is too much absorbent material in the densified areas, the product may delaminate when saturated. It can be seen that the absorbent material 102 is fully contained within the absorbent product 100 by the cover layer 106 and the densified areas 122. This reduces loss of the generally expensive absorbent material 102 during the processing, shipping, and handling of the products 100 prior to use.

The fibrous substrate 104 may have a cover layer 106 and a fibrous layer 108. The cover layer 106 may be a nonwoven fabric such as a spunbonded fabric, a thermal bonded fabric, a resin bonded fabric, and the like; an apertured film such as DRI-WEAVE, RETICULON, and the like; a densified top layer formed with hydrogen bonding; or any other suitable covering surface. The fibrous layer 108 may comprise cellulosic fibers, including wood pulp and cotton pulp; synthetic fibers, including polyolefins, polyesters, and bicomponent fibers; and the like. Useful absorbent structures and top surfaces are disclosed in Cancian et al., U.S. Pat. No. 4,592,943; Mays, et al. U.S. Pat. No. 4,713,134; Mays U.S. Pat. No. 4,787,947; Shimalla et al., U.S. Pat. No. 4,774,124; Luceri, EP-A-0 597 273; and the commonly assigned, copending application, Clark et al., U.S. Ser. No. 08/236, 762; the disclosures of which are herein incorporated by reference.

The absorbent material 102 may be formed of synthetic fibers, including spunbonded, melt blown card and bind staple fibers; cellulosic fibers such as wood pulp, stabilized wood pulp, peat moss; and superabsorbents. Useful superabsorbents include polyacrylates; modified natural and regenerated polymers such as polysaccharides; hydrocolloids such as modified polyacrylonitrile compounds; cross-linked nonionic polymers such as polyoxyethylene, polyoxypropylene and mixture thereof; derivatives of isobutylene-maleic anhydride copolymers; copolymers such as those disclosed in Le-Khac, U.S. Pat. Nos. 4,731,067; 4,743,244; 4,788,237; 4,813,945; 4,880,868; 4,892,533; and 5,151,465.

Preferably, the absorbent material 102 is a superabsorbent, more preferably, it is a superabsorbent powder, and most preferably, the absorbent material 102 is a particulate sodium polyacrylate superabsorbent, Aqua Keep J-550, available from Sumitomo Seika Chemical Company, Ltd. The absorbent material 102 can be applied to the moving web as necessary to provide the desired amount of absorbent material 102 to the resulting individual pads. Preferably, the absorbent material 102 is applied at about 100 to 1,000 mg/pad, more preferably about 200 to 800 mg/pad, and most preferably at about 400 to 600 mg/pad.

The barrier layer 112 may be formed of any barrier film useful in the disposable absorbent product art. Useful films include, without limitation, polyolefin films such as polyethylene and polypropylene; polyvinyl films such as polyvinyl acetate, polyvinyl chloride, and polyvinylidene chloride; copolymeric films such as ethylene-vinyl acetate, and blends or laminates of one or more of the above polymers. Preferred barrier films include ethylene-vinyl acetate/ polyethylene laminate films and polypropylene films. More preferably, the barrier film is a polyolefin such as polyethylene.

The selection of construction adhesive 110 and positioning adhesive 114 is not critical to the practice of the present invention. These adhesives may independently be chosen from solvent-releasing, e.g., emulsion or organic solvent based; curing, e.g., radiation cure, electron beam, or catalytic cure; or hot melt. Preferred adhesives include hot melt adhesives which may also be pressure sensitive adhesives (PSA). A representative, non-limiting list of useful adhesives includes those based on natural rubber, styrene/butadiene latex, A-B-A block copolymer, butyl rubber and polyisobutylene, acrylics including vinyl acetate-acrylate copolymers, vinyl ether polymers, polyalkene polymers, polyurethane, ethylene-vinyl acetate copolymers and polypropylene including atactic polypropylene. Preferably, the adhesive is an A-B-A block copolymer, an acrylic resin, or an ethylene-vinyl acetate copolymer. More preferably, the construction adhesive is based on an A-B-A block copolymer hot melt adhesive, such as National Starch #34-5539, and the positioning adhesive is an A-B-A block copolymer hot melt adhesive, such as H. B. Fuller Co. HL-1335.

The adhesive can be applied to the absorbent pad in any manner known to the ordinary practitioner. Such application methods include, without limitation, spraying, transfer coating, roll coating, slot coating, gravure rolling, etc.

Figure 7:
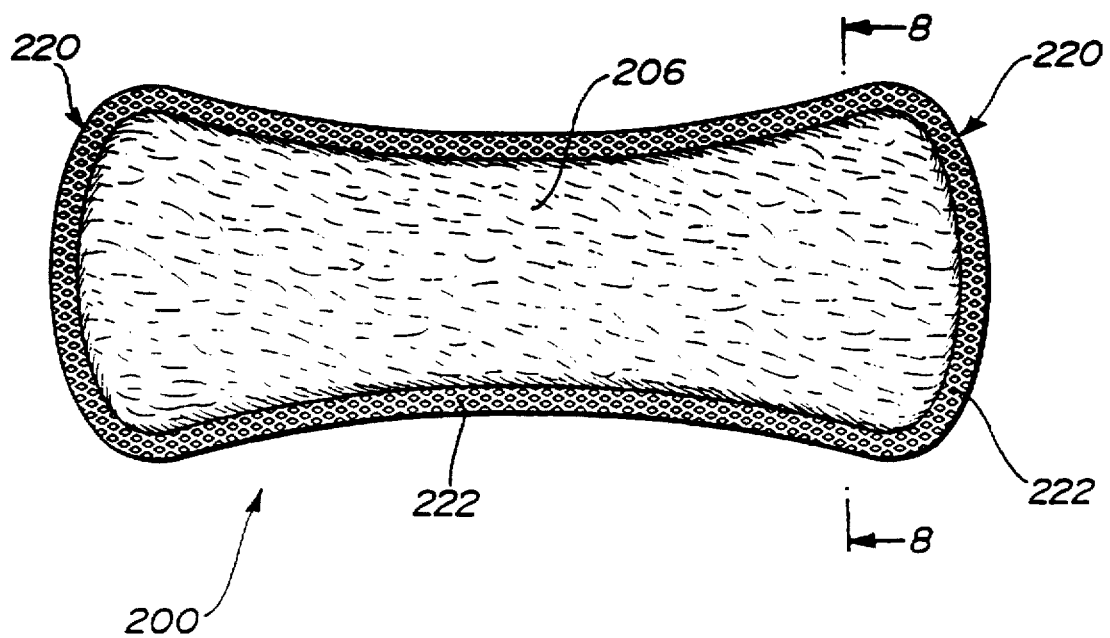
FIG. 7 is a perspective view of one embodiment of an absorbent product of the present invention.
Figure 8:
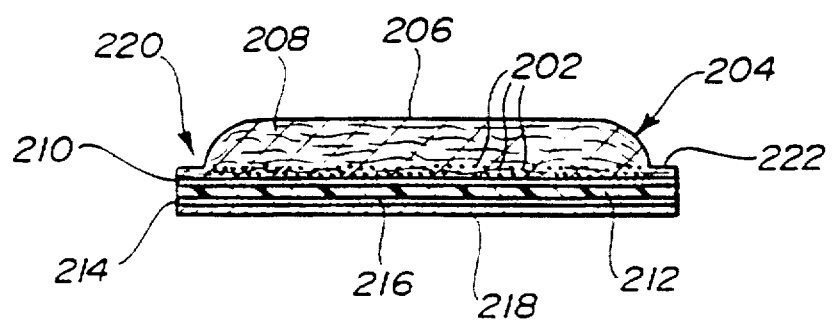
FIG. 8 is view along line 8—8 of FIG. 7, illustrating a laminated product which has a substantially absorbent material-free densification zone according to the present invention.

Referring now to FIGS. 7–8, there is illustrated a laminated absorbent product 200 having an absorbent material 202 distributed therein. The absorbent product 200 includes an absorbent structure 204 having a cover layer 206, a fibrous layer 208, and a construction adhesive 210. The absorbent structure 204 may be laminated to a barrier layer 212 having a positioning adhesive 214 disposed upon a garment-facing surface 216 thereof. The positioning adhesive 214 may be protected by a release liner 218.

At the peripheral edges 220 of the product 200, there is a densified area 222. This area 222 is substantially absorbent material-free. It can be seen that the absorbent material 202 is fully contained within the absorbent product 200 by the cover layer 206, the barrier layer 212, and the densified areas 222. This reduces loss of the generally expensive absorbent material 202 during the processing, shipping, and handling of the products 200 prior to use.

The fibrous substrate 204, cover layer 206, fibrous layer 208, barrier layer 212, absorbent material 202, positioning adhesive 214, and construction adhesive 210 may be selected from the materials listed above.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A continuous process for forming a laminated absorbent structure having reduced delamination tendencies comprising the steps of:

a) providing a moving fibrous substrate having lateral sides, a longitudinal axis, a first major surface, and a second major surface, opposite the first, the second major surface defined by a cover layer;

b) providing a pressure differential across the moving fibrous substrate, wherein fluid pressure acting on the first major surface is greater than the fluid pressure acting on the second major surface, thereby drawing air through the fibrous substrate;

c) masking at least a portion of the second major surface to air flow;

d) providing a metered amount of an absorbent material in an airstream to the first major surface in a pattern corresponding to the unmasked portion of the second major surface in a forming chamber having a pressure slightly less than atmospheric pressure; and e) densifying at least a portion of the fibrous substrate corresponding to the masked portion to laterally contain the absorbent material within the resulting absorbent structure.

2. The process of claim 1 further comprising the step of folding the fibrous substrate upon itself to provide an outer surface of the cover layer.

3. The process of claim 2 wherein the lateral sides of the fibrous substrate are folded parallel to the longitudinal axis to contain the absorbent material and to provide an outer surface of the cover layer.

4. The process of claim 1 further comprising the step of placing a containing layer over the first major surface to contain the absorbent material.

5. The process of claim 1 further comprising applying an adhesive composition to at least a portion of the first major surface of the fibrous substrate.

6. The process of claim 5 wherein the adhesive composition is applied to the substrate before the application of the absorbent material.

7. The process of claim 1 wherein the absorbent material provided to the first major surface is entrained into the air through the use of a venturi.

8. The process of claims 1, 3, or 6 wherein the adhesive composition adheres the absorbent material, the lateral sides of the fibrous substrate, and a central portion of the fibrous substrate together.

9. A continuous process for forming a laminated absorbent product having reduced delamination tendencies comprising the steps of:

a) providing a moving fibrous substrate having lateral sides, a longitudinal axis, a first major surface, and a second major surface, opposite the first, the second major surface defined by a cover layer;

b) applying an adhesive composition to at least a portion of the first major surface of the fibrous substrate;

c) providing a pressure differential across the moving fibrous substrate, wherein fluid pressure acting on the first major surface is greater than the fluid pressure acting on the second major surface, thereby drawing air through the fibrous substrate;

d) masking at least a portion of the second major surface corresponding to longitudinal product ends to air flow;

e) providing a metered amount of an absorbent material in an airstream to the first major surface in a pattern corresponding to the unmasked portion of the second major surface in a forming chamber having a pressure slightly less than atmospheric pressure;

f) folding lateral side portions of the fibrous substrate parallel to the longitudinal axis to contain the absorbent material, and to adhere the lateral side portions to a central portion, providing an absorbent structure having an outer surface of the cover layer;

g) attaching a barrier layer to one surface of the absorbent structure;

h) densifying at least a portion of the fibrous substrate corresponding to the masked portion to laterally contain the absorbent material within the absorbent structure; and i) separating individual laminated absorbent products at their longitudinal ends, leaving a densified portion at the longitudinal end of each product.

10. The process of claim 1 wherein the absorbent material comprises powdered superabsorbent material.

11. The process of claim 9 wherein the absorbent material provided to the first major surface is entrained into the air through the use of a venturi.

* * * * *